United States Patent
Weber

(10) Patent No.: US 10,016,146 B2
(45) Date of Patent: Jul. 10, 2018

(54) MAGNETIC PARTICLE IMAGING METHOD

(71) Applicant: Bruker BioSpin MRI GmbH, Ettlingen (DE)

(72) Inventor: Alexander Weber, Karlsruhe (DE)

(73) Assignee: Bruker BioSpin MRI GmbH, Ettlingen (DE)

( * ) Notice: Subject to any disclaimer, the term of this patent is extended or adjusted under 35 U.S.C. 154(b) by 38 days.

(21) Appl. No.: 15/208,632

(22) Filed: Jul. 13, 2016

(65) Prior Publication Data

US 2017/0020407 A1    Jan. 26, 2017

(30) Foreign Application Priority Data

Jul. 24, 2015 (DE) .................. 10 2015 214 071

(51) Int. Cl.
*A61B 5/05* (2006.01)
*A61B 5/00* (2006.01)
*G01R 33/12* (2006.01)

(52) U.S. Cl.
CPC .......... *A61B 5/0515* (2013.01); *A61B 5/7203* (2013.01); *A61B 5/7257* (2013.01); *G01R 33/1276* (2013.01)

(58) Field of Classification Search
None
See application file for complete search history.

(56) References Cited

U.S. PATENT DOCUMENTS

2011/0221438 A1* 9/2011 Goodwill ............... G01R 33/10
324/301

2011/0246103 A1* 10/2011 Rahmer .................. A61B 5/05
702/57

(Continued)

FOREIGN PATENT DOCUMENTS

DE   10 2012 211 662      1/2014
WO   WO2014005658 A1 *   1/2014

OTHER PUBLICATIONS

Tobias Knopp et al., "2D model-based reconstruction . . . ", Med. Phys. 37(2), Feb. 2010.

(Continued)

*Primary Examiner* — Amanda Lauritzen Moher
*Assistant Examiner* — Shahdeep Mohammed
(74) *Attorney, Agent, or Firm* — Paul Vincent

(57) ABSTRACT

An MPI method determines calibration and measurement volumes, wherein the calibration volume is larger than the measurement volume and the overall measurement volume is arranged within the calibration volume. Calibration signals are detected and a system matrix S is created. An MPI measuring signal u is recorded, a location-dependent magnetic particle concentration c with magnetic particle concentration values $c_i$ within the calibration volume is reconstructed and the magnetic particle concentration values $c_i$ are associated with voxels in the calibration volume. Magnetic particle concentration values $c_i$ which were associated with voxels outside of the measurement volume are discarded and an MPI image is generated which exclusively contains magnetic particle concentration values $c_i$ which were associated with the voxels within the measurement volume. MPI image data are thereby generated with little artifacts within a short time even in case of high magnetic particle densities outside of the measurement volume.

12 Claims, 8 Drawing Sheets

(56) References Cited

U.S. PATENT DOCUMENTS

| | | | |
|---|---|---|---|
| 2012/0153948 A1* | 6/2012 | Rahmer | A61B 5/0515 324/301 |
| 2012/0153949 A1* | 6/2012 | Biederer | A61B 5/05 324/301 |
| 2015/0221103 A1 | 8/2015 | Knopp | |

OTHER PUBLICATIONS

B. Gleich et al., "Experimental results . . . ", Phys. Med. Biol. 53 (2008) N81-N84.

J. Weizenecker et al., "Three-dimensional-real-time . . . ", Phys. Med. Biol. 54 (2009) L1-L10.

* cited by examiner

MAGNETIC PARTICLE IMAGING METHOD

This application claims Paris convention priority from DE 10 2015 214 071.7 filed Jul. 24, 2015 the entire disclosure of which is hereby incorporated by reference.

BACKGROUND OF THE INVENTION

The invention concerns an MPI method for localizing magnetic particles within a test sample, wherein a location-dependent magnetic field is applied which has a field-free region, the method comprising the following steps:

determining a calibration volume and a measurement volume, wherein the calibration volume is larger than the measurement volume and wherein the overall measurement volume is arranged within the calibration volume;

detecting calibration signals $S_j$ and creating a system matrix S from the calibration signals $S_j$;

recording an MPI measuring signal u (MPI time signal or MPI frequency spectrum obtained through Fourier transformation of the MPI time signal), wherein through application of the magnetic control field, the field-free region is moved through the measurement volume by means of a measuring sequence;

reconstruction of a location-dependent magnetic particle concentration with magnetic particle concentration values $c_i$ within the calibration volume from the recorded MPI measurement signal u and the created system matrix S and association of the magnetic particle concentration values $c_i$ with voxels in the calibration volume.

A method of this type is disclosed e.g. in [01]-[03].

Magnetic particle imaging (abbreviated as "MPI") is an imaging method which permits determination of the local distribution of superparamagnetic nanoparticles (in the present case designated as magnetic particles). Towards this end, the magnetic particles are exposed to different static and dynamic magnetic fields in a measurement volume and the magnetization changes of the magnetic particles are detected by means of receiver coils. For spatial encoding in MPI, a magnetic gradient field is applied in the region of the measurement volume which has a field-free region. The field-free region is shifted along a pre-defined trajectory (predetermined dependence of each point of the field-free region) within the measurement volume by means of a dynamic magnetic field (drive field) and/or homogeneous focus fields. By sweeping over the magnetic particles with the field-free region and the associated magnetization change, a measuring signal is generated which is detected by receiver coils.

A system matrix is generated for calibration of the system. For this purpose, a calibration measurement can e.g. be performed, in which a calibration signal is recorded for each measuring point and is stored in the system matrix. The calibration measurement is also performed for positions of the calibration sample outside of the measurement volume, which allows reconstruction of an MPI image of an overall volume which is larger than the measurement volume.

Whereas in [01] and [02] MPI measurements are performed on a phantom with magnetic particles, in which all magnetic particles are located within the measurement volume, [03] describes a method for in vivo recording of a rat heart. During in vivo recordings, magnetic particles are also located outside of the measurement volume. Although these are not swept over by the field-free region, they nevertheless contribute to the measurement signal due to their rotation and unsharpness of the field-free region. This can lead to artefacts in the MPI image.

[04] describes a calibration method for an MPI apparatus, wherein the calibration method comprises m calibration MPI measurements with a calibration sample and generates from these an image reconstruction matrix by means of which the signal contributions of N voxels within a volume under investigation of the MPI apparatus are determined, wherein compressed-sensing-steps are applied using a transformation matrix, which sparsifies the image reconstruction matrix and only a number M<N of calibration MPI measurements for M voxels are performed, from which the image reconstruction matrix is created and stored. In this connection, the volume of the calibration sample may be larger than the volume of one voxel.

It is the underlying purpose of the present invention to propose a method, in particular for in vivo MPI recordings, by means of which low-artefact image data can be generated even with high magnetic particle densities outside of the measurement volume and in a time-saving fashion.

SUMMARY OF THE INVENTION

This object is achieved in accordance with the invention with a method in accordance with the independent claim.

Both the measurement volume and the calibration volume comprise a plurality of voxels (volume units), wherein the size of a voxel is determined by the separations of the calibration sample positions which are used for calibration of the measurement volume. For a preferred application, the size of a voxel corresponds to the size of the calibration sample and the calibration sample position corresponds to the center of the voxel.

In accordance with the invention, those magnetic particle concentration values, which were associated with voxels outside of the measurement volume, are discarded and an MPI image is generated which exclusively contains magnetic particle concentration values which were associated with voxels of a voxel grid within the measurement volume.

Time signals can be detected as calibration signals or frequency spectra can be obtained from time signals through Fourier transformation.

In order to minimize the influence of magnetic particles localized outside of the measurement volume on the measurement result, calibration signals for sample positions outside of the measurement volume are also detected ("overscanning"). However, in contrast to prior art, those reconstructed magnetic particle concentration values, which were associated with voxels outside of the measurement volume, are discarded and an MPI image is generated which exclusively contains magnetic particle concentration values which were associated with the voxels within the measurement volume.

Within the scope of the invention, it was found out that for reconstruction using a calibration volume which was selected to be larger than the measurement volume, particle signals of magnetic particles outside of the measurement volume are projected to the outer border of the measurement volume independently of their actual position such that after reconstruction, a misinterpretation of the overscan area (area of the calibration volume outside of the measurement volume) might occur. The inventive "overscanning" during detection of the calibration signals (calibration volume>measurement volume) and reconstruction of the overall calibration volume in combination with discarding the magnetic particle concentration values for voxels outside of the measurement volume ensure that the influence of the magnetic particles located outside of the measurement volume on MPI signals within the measurement volume is taken into consideration. Moreover, the influence of the magnetic particles located outside of the measurement volume on reconstructed data outside of the measurement volume does not enter the MPI image which is used for further evaluation/interpretation. For this reason, the MPI image contains only reliable MPI data (magnetic particle concentration values).

The magnetic particle concentration values outside of the measurement volume can be discarded prior to or after generation of an image file. It is decisive that the magnetic particle concentration values associated with the voxels outside of the measurement volume are not detected in the MPI image used for further evaluation in order to prevent misinterpretation of the data contained in the MPI image.

The measurement volume is selected in a user-defined fashion and is defined through excitation field and/or gradient fields and/or focus fields in dependence on the coil topography.

The field-free region may e.g. be a field-free point or a field-free line which is moved through the measuring sequence along a trajectory through the measurement volume.

The inventive method is particularly advantageous when particle concentrations of areas are to be determined, which are larger than the measurement volume. Towards this end, a plurality of MPI measurements must be performed, wherein the measurement volume must be correspondingly shifted and the overall measurement volumes form the area to be measured. In accordance with the invention, the reconstructed magnetic particle concentration values outside the measurement volume must not enter the finally determined location-resolved magnetic particle concentration illustrated as an MPI image. For recording a plurality of adjacent measurement volumes, the calibration volumes must be selected in accordance with the invention in such a fashion that they overlap (around the overscan area).

The calibration volume advantageously surrounds the measurement volume, i.e. the calibration volume projects past the measurement volume in all directions. In this fashion, magnetic particles, which are located on different sides outside of the measurement volume, are equally taken into consideration.

In one particularly preferred variant of the inventive method, the calibration volume projects past the measurement volume in each direction by one single voxel in each case. The time required for calibration and reconstruction can therefore be minimized. In particular, in case of a small ratio between the magnetic particle concentration outside of the measurement volume and the magnetic particle concentration inside the measurement volume, no substantial improvement is achieved due to the noise that occurs during the measurement in case a larger overscan is selected such that an overscan with a thickness of one single voxel is sufficient.

In one preferred variant of the inventive method, the calibration signals in the area outside of the measurement volume are detected with a lower resolution than inside the measurement volume. The overscan area can therefore be scanned in a timesaving fashion.

This can be achieved e.g. in that in an area outside of the measurement volume fewer calibration signals are recorded than voxel positions present in this area. For this reason, calibration signals are not detected for all voxels outside of the measurement volume. The voxel grid of the measurement volume may thereby be extended to the overall calibration volume (identical voxel grid for measurement volume and overscan area).

Alternatively or additionally, a larger calibration sample may be used for detecting the calibration signals outside of the measurement volume than for detecting the calibration signals inside the measurement volume.

Moreover, for detecting the calibration signals outside of the measurement volume another voxel grid may be used, in particular a voxel grid with larger voxels than those used for detecting the calibration signals within the measurement volume. A change of the voxel grid in the overscan area means that the calibration sample is shifted to other calibration sample positions. In this case, the voxel grid is thus adjusted to the desired resolution in the overscan area.

It is also feasible to provide all three measures for detecting the calibration signals outside of the measurement volume, i.e. to use a larger calibration sample, adjust the voxel grid and record fewer calibration signals than there are voxel positions in this area.

The method is advantageously used for measuring those test samples which have at least one area neighboring the measurement volume in which a magnetic particle concentration prevails which is larger than zero (i.e. there are magnetic particles outside of the measurement volume, e.g. in in vivo measurements) preferably larger or equal to the magnetic particle concentration in the measurement volume. In particular, in the latter case, the influence of the magnetic particles both on areas inside of the measurement volume and also on areas of the calibration volume outside of the measurement volume is large. For this reason, considerable artefacts can occur with conventional methods.

For detecting the calibration signals, a calibration measurement is advantageously performed, wherein for different positionings of the calibration sample within the calibration volume, one calibration signal $S_j$ is detected in each case, wherein the field-free region is moved through the measurement volume during detection of each calibration signal $S_j$ through application of the magnetic control field in accordance with the measuring sequence.

For calibration of the system matrix, a calibration sample is moved to different voxel positions and the system response (calibration signal $S_j$) is measured in each case. Due to temperature effects, drifts at the individual frequencies of the calibration signals may occur at the start of measurement. In accordance with the invention, the reconstructed values for voxels outside of the measurement volume are discarded again after reconstruction, and for this reason it is advantageous for the calibration measurement to first measure the calibration signals for sample positions outside of the measurement volume and subsequently the calibration signals for sample positions inside the measurement volume. The drift effects do not have a substantial effect on the MPI image in this case.

The inventive method is advantageously used for in vivo recordings. Here, the invention is particularly advantageous, since in case of in vivo recordings there is normally a magnetic particle concentration outside of the measurement volume which cannot be neglected.

DESCRIPTION OF THE PREFERRED EMBODIMENT

Figure 1:
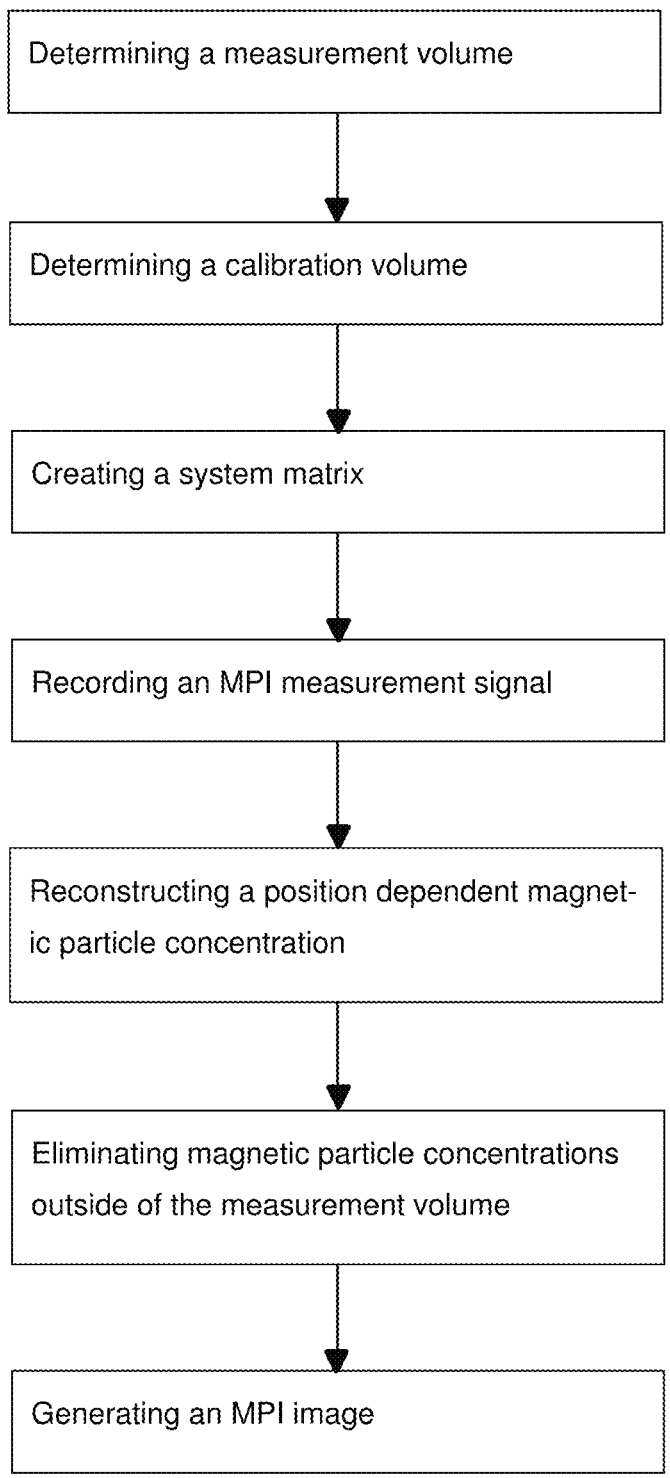
FIG. 1 shows a flow chart of the inventive method.

The process steps of the inventive method given in FIG. 1 are described below:

At first, a user-defined measurement volume and a voxel grid for the measurement volume are selected, in which a field-free region is moved over the individual voxels of the voxel grid of the measurement volume during subsequent MPI measurement. Towards this end, corresponding magnetic fields (gradient fields, excitation fields, focus fields) are applied, wherein the size of the measurement volume depends on the amplitude of these magnetic field, or the magnetic fields are adjusted such that the desired size of the measurement volume is obtained.

For establishing a system matrix, calibration is performed within a previously selected calibration volume which is larger than the measurement volume (calibration volume=measurement volume+overscan area) and contains it. A voxel grid different from the voxel grid of the measurement volume can then be selected for the overscan area or the voxel grid of the measurement volume can be expanded to the overall calibration volume. Calibration may be performed through simulation or through calibration measurement. For a calibration measurement, a small sample (calibration sample) filled with magnetic particles is used, wherein in particular different calibration samples can be used for detecting the calibration signals inside and outside of the measurement volume. The calibration sample is moved e.g. by means of a positioning robot to the different positions within the calibration volume. Instead of moving the calibration sample, the magnetic ratios of different sample locations can be simulated by means of additional magnetic fields. Omission of robot movement reduces the calibration time. For each calibration sample position in the calibration volume, a calibration signal is recorded under the same conditions (the same measuring sequence) as in the actual MPI measurement (recording of the measuring signals). Thus, calibration signals $S_j$ are recorded for each measuring point inside the measurement volume and for additional measuring points outside of the measurement volume. The system matrix S is then produced from the calibration signals by entering the individual calibration signals $S_j$, i.e. the individual frequency spectra or the individual time signals, column by column.

The actual MPI measurement is subsequently performed by recording an MPI signal (measurement vector u), whereas the field-free region passes through the measurement volume in accordance with the measurement sequence.

Within the scope of reconstruction, a magnetic particle concentration vector c is then determined through solving the linear equation system u=S·c by means of the determined system matrix S and the measurement vector u. This means, a location-dependent concentration distribution with magnetic particle concentration values $c_i$ (magnetic particle distribution) is reconstructed for the overall calibration volume, wherein the local dependence of the magnetic particle concentration values $c_i$ is derived from the system matrix S.

In accordance with the invention, those magnetic particle concentration values $c_i$, which were associated with areas (voxels) outside of the measurement volume, are discarded.

Only then is the MPI image created, namely exclusively for magnetic particle concentration values $c_i$ which were associated with voxels inside the measurement volume. For this reason, the resulting MPI image exclusively contains particle concentration values $c_i$ for voxels inside the measurement volume.

In accordance with the invention, it turned out that the magnetic particle concentration values contained in a prior art MPI image contain artefacts outside of the measurement volume, in particular in recordings of a measuring volume, which is located next to an area having a high magnetic particle density. The inventive method ensures that the influence of magnetic particles outside of the measurement volume on the measuring signals inside the measurement volume is taken into consideration. Moreover, it is ensured that the magnetic particle concentration values determined for voxels outside of the measurement volume are not used for further calculations or measurements since they are not reliable.

Figure 2:
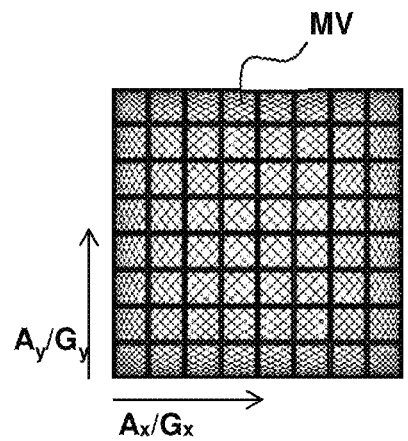
FIG. 2 shows a measurement volume with a Lissajous trajectory (2D illustration)

FIG. 2 shows a measurement volume MV with a Lissajous trajectory along which a field-free point is moved through the measurement volume MV by means of a drive field (superposition of a sinusoidal excitation field A and a gradient field G). The measurement volume MV is divided into voxels.

Figure 3:
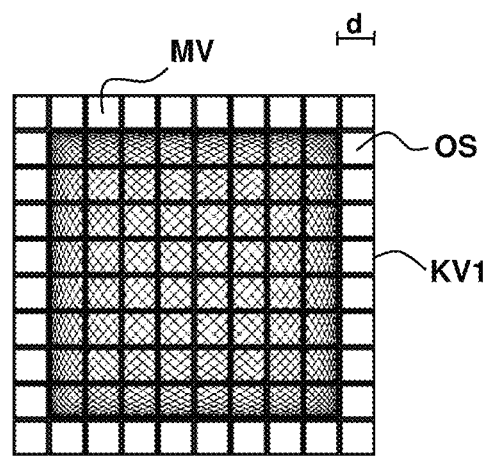
FIG. 3 shows the measurement volume of FIG. 2 and a calibration volume with an overscan of one single voxel row (2D illustration)
Figure 4:
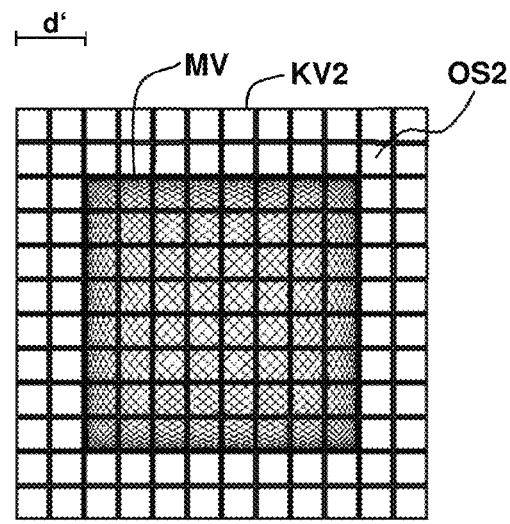
FIG. 4 shows the measurement volume of FIG. 2 and a calibration volume with one overscan of two voxel rows (2D illustration)
Figure 5:
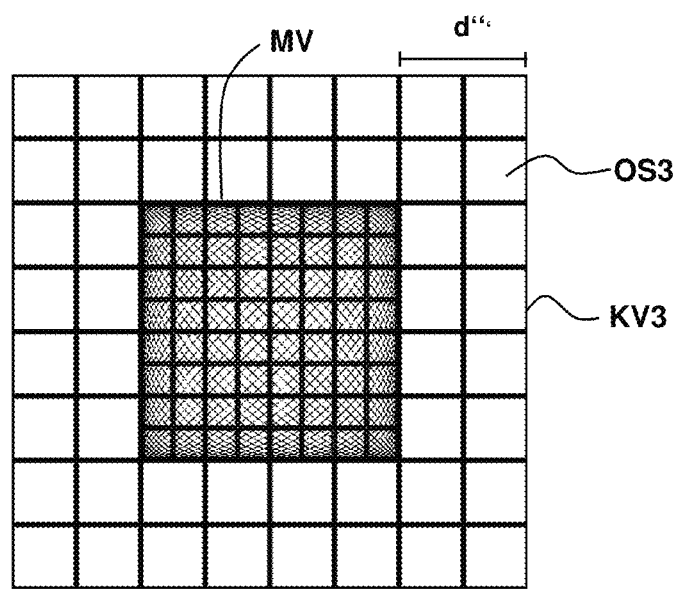
FIG. 5 shows the measurement volume of FIG. 2 and a calibration volume with an overscan of two voxel rows (with respect to the voxel grid of the overscan area), wherein a voxel grid with half resolution is used outside of the measurement volume. The size of the calibration sample is adjusted to the voxel size such that a calibration sample is used for the overscan area which is four times larger than in the measurement volume (2D illustration)

FIGS. 3 to 5 show the measurement volume MV of FIG. 2 with different calibration volumes KV1, KV2, KV3 which overlap the measurement volume MV on all sides, thereby forming an envelope. The overlap of the calibration volume (overscan area OS1, OS2, OS3) beyond the measurement volume MV thus forms an envelope of the measurement volume MV.

FIG. 3 shows a particularly preferred selection of the calibration volume KV1. In this case, one single additional voxel row (2D measurement) which projects past the measurement volume MV is recorded (overscan area OS1) in the calibration step in addition to the measurement volume V. In case of a 3D measurement, the overscan area OS1 comprises an envelope of the measurement volume MV with a thickness d of one single voxel. Experimental measurements have shown that this is often sufficient in order to eliminate the contribution of all magnetic particles outside the measurement volume MV in the system matrix method for image reconstruction.

FIG. 4 shows an alternative variant of selection of the calibration volume KV2. In this case, the calibration volume KV2 projects past the measurement volume MV by two voxel rows, wherein the voxel size is defined by the separations of the calibration sample positions in the measurement volume MV. The overscan area OS2 thus has a thickness d' of two voxels.

It has surprisingly turned out that it is not required to measure the complete area outside of the measurement volume containing magnetic particles within the scope of the calibration measurement in order to obtain a reliable result. It was namely found out that all magnetic particles in the area outside of the measurement volume MV project a similar image to the transition between measurement volume MV and overscan area OS1, OS2, OS3. The overscan area OS1, OS2, OS3 can therefore be scanned with a lower resolution than the measurement volume MV without losing essential information. For example, FIG. 5 shows an overscan area OS3 which comprises two voxel rows (relative to the voxel grid of the overscan area OS3), wherein in this case a different voxel grid was used for the overscan area than for the measurement volume. A voxel of the voxel grid of the overscan area (OS voxel—in FIG. 5 illustrated as large squares in the overscan area OS3) corresponds to four voxels of the voxel grid of the measurement volume) (d"=4 voxels of the voxel grid of the measurement volume). For each OS voxel only one single calibration signal is recorded, i.e. the overscan area OS3 is in this case either measured with a calibration sample which is larger (in the present case 2×2 voxels) than the calibration sample by means of which the measurement volume MV is measured (1 voxel) and/or the calibration sample is measured within the section of the 2×2 voxels at any position (e.g. at one of the four voxel positions of the OS voxel or in the center of the OS voxel).

Simulation data relating to different overscan areas are shown below: MPI data for a 2D measuring sequence were simulated. The voxel size corresponds to 1×1 mm$^2$ and the measurement volume is 32×32 mm$^2$.

Figure 6:
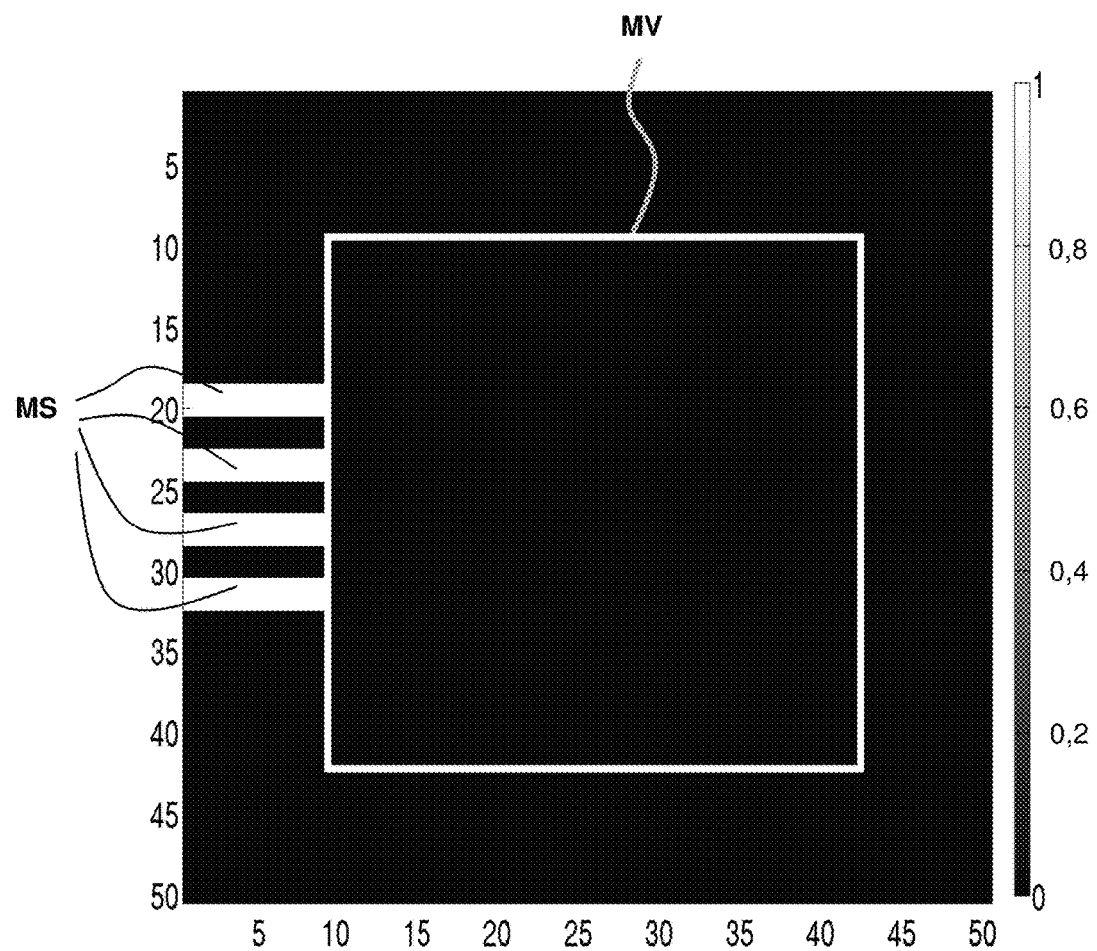
FIG. 6 shows a reference image of a magnetic particle distribution for simulation.

FIG. 6 shows a reference image of a simulation of the inventive method for the extreme case of a particle density of zero within the measurement volume MV. Four magnetic particle strips MS are arranged outside of the measurement volume MV with 2×9 voxels each and with the intensity 1 bordering the left-hand side of the measurement volume. An intensity of 1 means in this case that the same amount of magnetic particles is located in this voxel during object measurement as was located in the calibration sample during calibration measurement (relative intensity related to calibration measurement). The magnetic particle density in this case is thus considerably larger outside of the measurement volume MV than inside the measurement volume MV.

Figure 7:
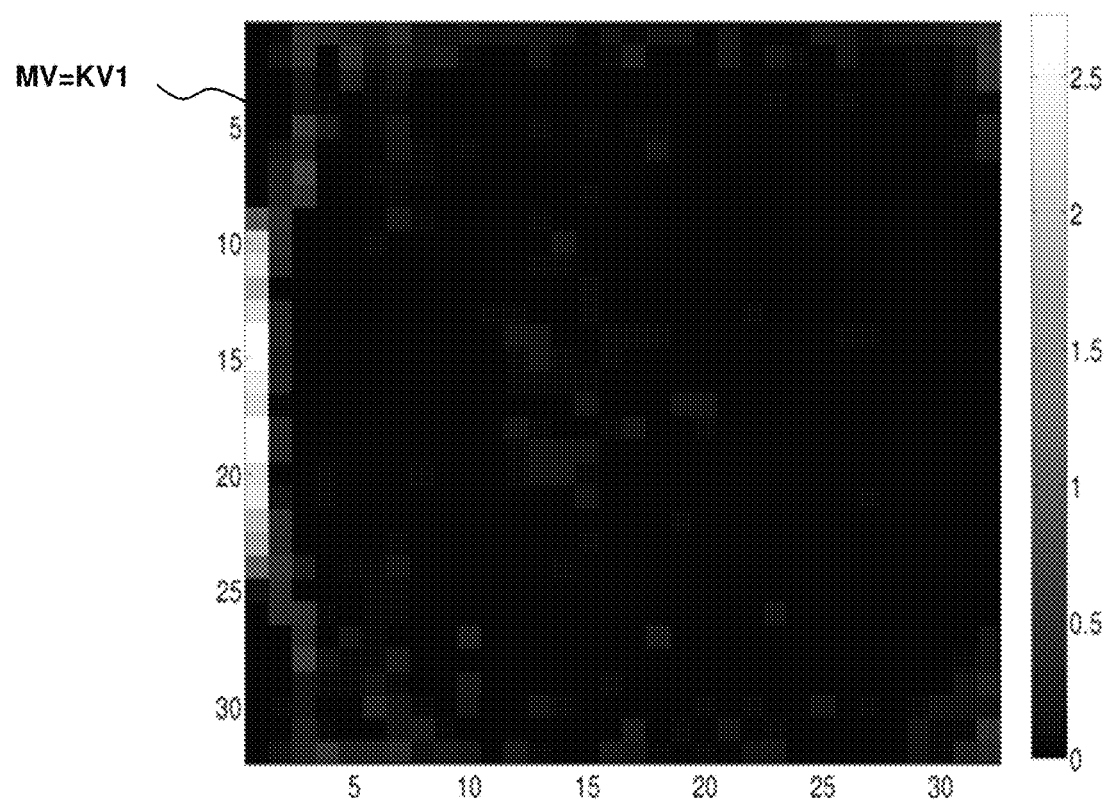
FIG. 7 shows the simulation data of the magnetic particle distribution of FIG. 6 without overscan.
Figure 8:
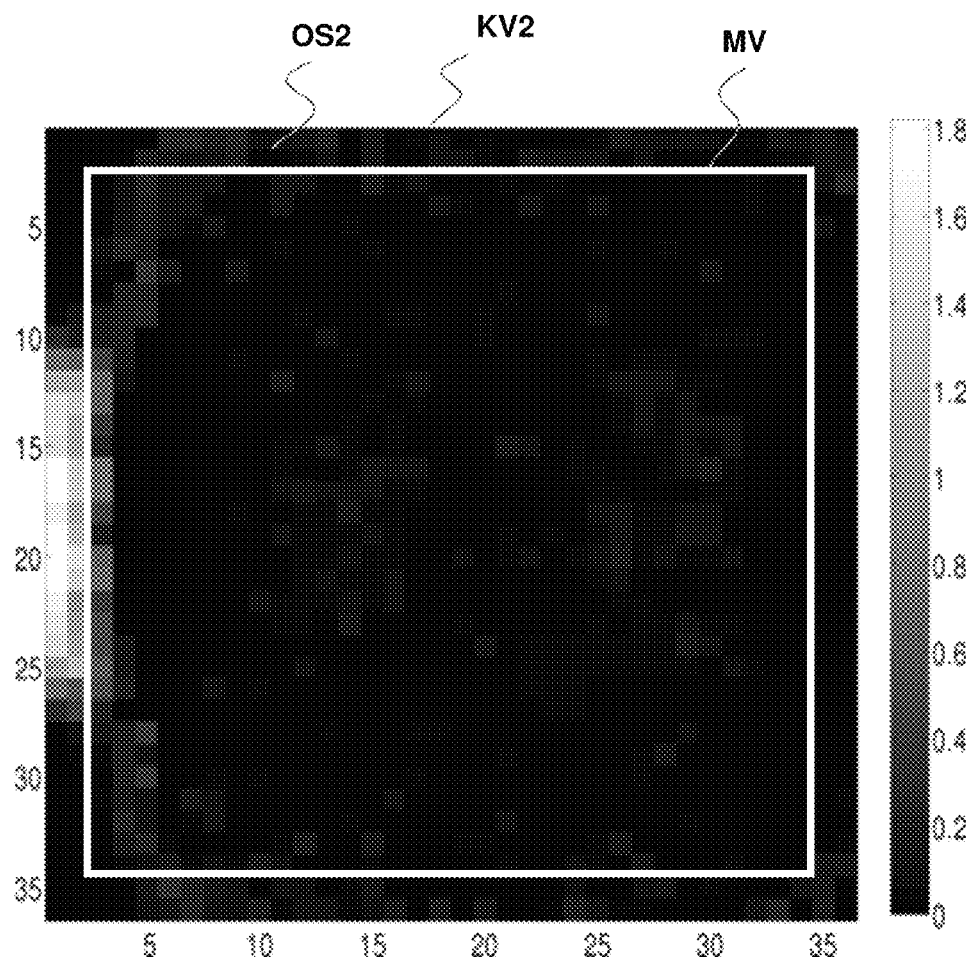
FIG. 8 shows simulation data of the magnetic particle distribution of FIG. 6 with an overscan of two voxel rows.
Figure 9:
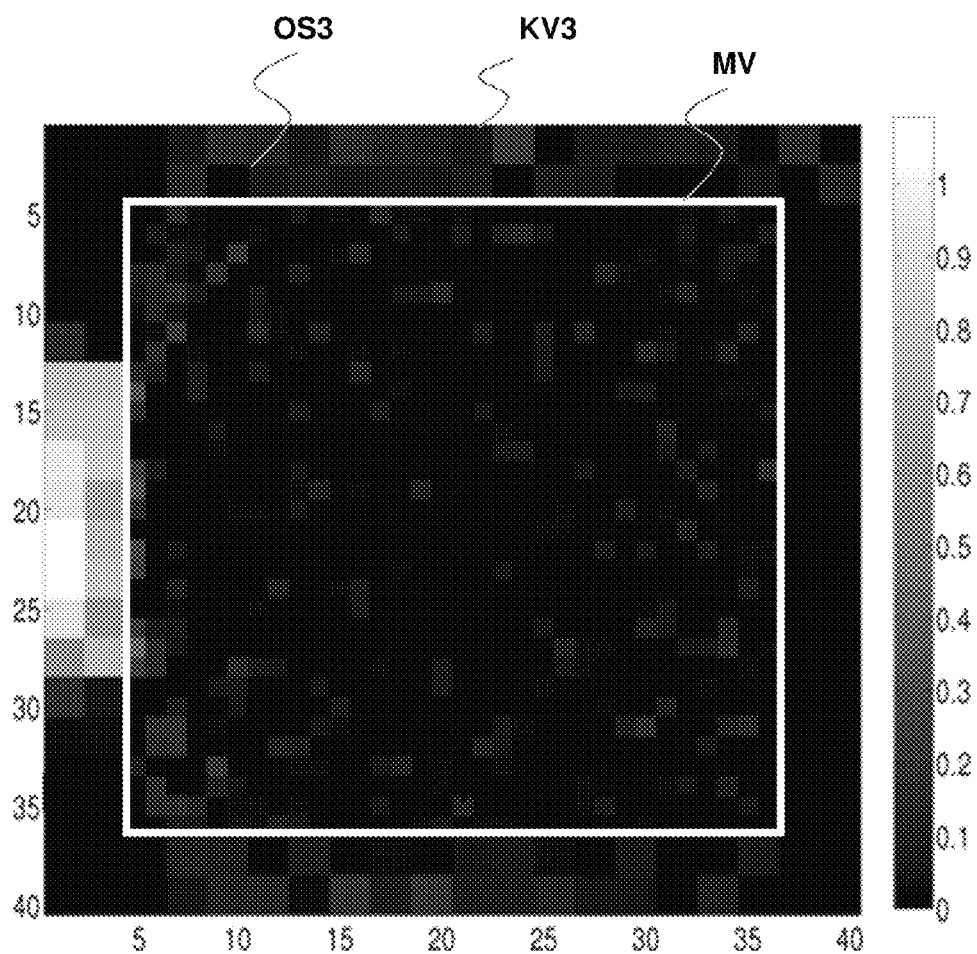
FIG. 9 shows simulation data of the magnetic particle distribution of FIG. 6 with an overscan of two voxel rows (with respect to the voxel grid of the overscan area) wherein in the overscan area a voxel grid with half resolution is used. The size of the calibration sample is adjusted to the voxel size such that a calibration sample is used for the overscan area which is four times larger than in the measurement volume.

FIGS. 7 to 9 show simulated image data wherein the overscan area OS2, OS3 was varied. In all cases, the overscan area OS2, OS3 was smaller than the area within which the totality of all magnetic particles was arranged. Each of the image data illustrated in FIGS. 7-9 covers the overall calibration volume KV1, KV2, KV3, i.e. contains all data obtained from reconstruction.

FIG. 7 shows simulated reconstructed data without overscan (calibration volume KV=measurement volume MV). One can clearly see that artefacts of high intensity (>2.5) occur at the left-hand edge within the measurement volume.

Figure 10:
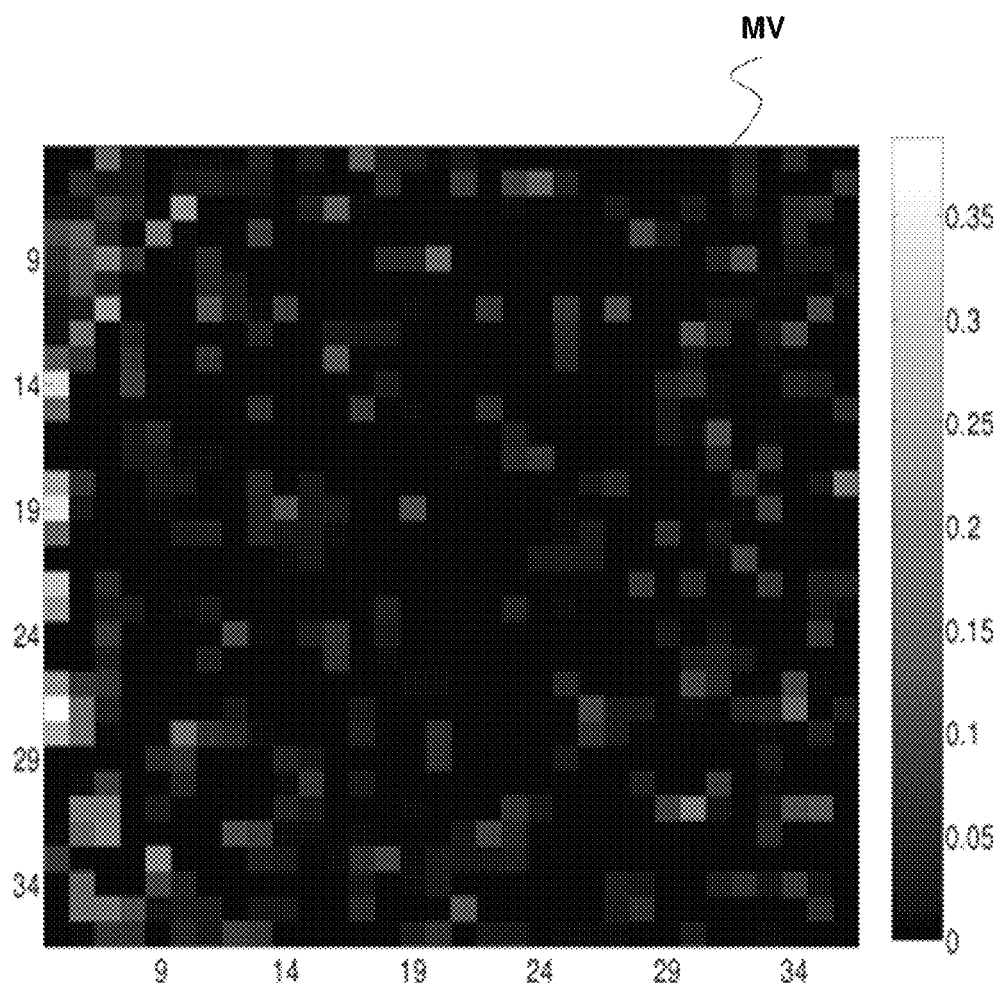
FIG. 10 shows the result of the inventive method with an overscan in accordance with FIG. 9.

FIGS. 8 and 9 show simulated reconstructed data with an overscan of two voxel rows (FIG. 8) or two OS voxel rows and one OS voxel size of four voxels (FIG. 9). The projection of the external magnetic particle distribution into the measurement volume is considerably reduced in FIG. 8 and hardly noticeable in FIG. 9. The overscan areas OS2, OS3 show an area with a high signal intensity which, however, does not illustrate the real magnetic particle distribution. The reconstructed data for the overscan areas OS2, OS3 are therefore to be regarded as not reliable. In accordance with the inventive method, the data reconstructed for the overscan area OS2, OS3 are discarded such that the magnetic particle distribution illustrated in FIG. 10 is obtained as result of the MPI measurement (MPI image) (instead of the magnetic particle distribution illustrated in FIG. 9).

For this reason, reliable MPI data can be obtained with the inventive method even for measurement volumes which are surrounded by areas with high magnetic particle density.

LIST OF REFERENCES

[01] T. Knopp, S. Biederer, T. F. Sattel, J. Rahmer, J. Weizenecker, B. Gleich, J. Borgert, T. M. Buzug: "2D model-based reconstruction for magnetic particle imaging"; Medical Physics, 37(2):485-491, 2010

[02] B. Gleich, J. Weizenecker, J. Borgert: "Experimental results on fast 2D-encoded magnetic particle imaging" Physics in Medicine and Biology, 53(6):N81-N84, March 2008

[03] J. Weizenecker, B. Gleich, J. Rahmer, H. Dahnke, J. Borgert: "Three-dimensional real-time in vivo magnetic particle imaging": Physics in Medicine and Biology, 54(5):L1-L10, 2009

[04] DE 10 2012 211 662 A1

LIST OF REFERENCE NUMERALS d, d', d" thickness of the overscan area
KV, KV1, KV2, KV3 calibration volume
MS magnetic particle strip
MV measurement volume
OS2, OS3 overscan area

I claim:

1. An MPI (magnetic particle imaging) method for localizing magnetic particles within a test sample, the method comprising the steps of:
   a) generating a location-dependent magnetic field having a field-free region;
   b) defining a calibration volume, the calibration volume being subdivided into a matrix of calibration volume voxels having an outer calibration volume border;
   c) defining a measurement volume, the measurement volume being subdivided into a matrix of measurement volume voxels having an outer measurement volume border which lies within the outer calibration volume border and which is separated from that outer calibration volume border by a peripheral ring of calibration volume voxels;
   d) detecting calibration signals $S_j$ at a plurality of calibration volume voxels and including calibration volume voxels located within the peripheral ring of calibration volume voxels;
   e) creating a system matrix S from the calibration signals $S_j$ detected in step d);
   f) recording an MPI measuring signal u from the test sample at a calibration volume voxel;
   g) applying a magnetic control field in order to move the field-free region;

h) repeating steps f) and g) until the field free region is moved throughout the calibration volume in a measuring sequence;

i) reconstructing a location-dependent magnetic particle concentration c of magnetic particle concentration values $c_i$ within the test sample throughout the calibration volume using the MPI measurement signals recorded in steps f) and the system matrix S created in step e);

j) mapping the magnetic particle concentration values $c_i$ to the calibration volume voxels;

k) discarding magnetic particle concentration values $c_i$ which are mapped to calibration volume voxels located within the peripheral ring of calibration volume voxels; and l) generating an MPI image which exclusively contains magnetic particle concentration values $c_i$ which were mapped to voxels of a voxel grid within the outer measurement volume border.

2. The method of claim 1, wherein a calibration measurement is performed for detecting the calibration signals, with one calibration signal $S_j$ being detected in each case for different positionings of the calibration sample within the calibration volume, wherein the field-free region is moved through the measurement volume during detection of each calibration signal $S_j$ through application of the magnetic control field in accordance with a measuring sequence.

3. The method of claim 1, wherein the method is used for in vivo recordings.

4. The method of claim 1, wherein the calibration volume surrounds the measurement volume.

5. The method of claim 4, wherein the calibration volume projects past the measurement volume in each direction by one voxel in each case.

6. The method of claim 1, wherein the calibration signals are detected with a lower resolution in an area outside of the measurement volume than inside the measurement volume.

7. The method of claim 6, wherein fewer calibration signals are recorded in an area outside of the measurement volume than voxel positions present in that area.

8. The method of claim 6, wherein a larger calibration sample is used for detecting the calibration signals outside of the measurement volume than for detecting the calibration signals inside the measurement volume.

9. The method of claim 6, wherein a different voxel grid is used for detecting the calibration signals outside of the measurement volume than for detecting the calibration signals inside the measurement volume.

10. The method of claim 1, wherein the method is used for measuring test samples having at least one area next to the measurement volume with a magnetic particle concentration which is larger than zero.

11. The method of claim 10, wherein the magnetic particle concentration is larger than or equal to a magnetic particle concentration in the measurement volume.

12. The method of claim 11, wherein the calibration signals are first measured for sample positions outside of the measurement volume and subsequently for sample positions inside the measurement volume.

* * * * *